(12) United States Patent
Kido

(10) Patent No.: US 9,693,674 B2
(45) Date of Patent: Jul. 4, 2017

(54) RIGID ENDOSCOPE WITH HERMETIC SEAL

(71) Applicant: FUJIFILM Corporation, Tokyo (JP)

(72) Inventor: Takashi Kido, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 372 days.

(21) Appl. No.: 14/615,014

(22) Filed: Feb. 5, 2015

(65) Prior Publication Data

US 2015/0245763 A1 Sep. 3, 2015

(30) Foreign Application Priority Data

Feb. 28, 2014 (JP) ................................ 2014-038851

(51) Int. Cl.
*A61B 1/00* (2006.01)
*A61B 1/05* (2006.01)
*A61B 1/04* (2006.01)

(52) U.S. Cl.
CPC ........ *A61B 1/0011* (2013.01); *A61B 1/00124* (2013.01); *A61B 1/051* (2013.01)

(58) Field of Classification Search
CPC ... A61B 1/00071; A61B 1/05; A61B 1/00114; A61B 1/0011; A61B 1/051; A61B 1/00124

USPC .......................................... 600/121–123, 138
See application file for complete search history.

(56) References Cited

FOREIGN PATENT DOCUMENTS

JP 7-39515 A 2/1995

*Primary Examiner* — Timothy J Neal
(74) *Attorney, Agent, or Firm* — Birch, Stewart, Kolasch & Birch, LLP

(57) ABSTRACT

A rigid endoscope includes an imaging module and a hermetic shell for containing the imaging module. A connecting line is contained in the hermetic shell, and has first and second ends. The first end is connected to the imaging module. A receiving opening is formed in the hermetic shell. A female tapered surface is formed inside the receiving opening. A sealed terminal device is connected electrically with the second end of the connecting line, for hermetically closing the receiving opening. A male tapered surface is formed on the sealed terminal device, for retaining the sealed terminal device in the receiving opening by engagement with the female tapered surface, to keep the hermetic shell air-tight. Preferably, the male and female tapered surfaces are attached together by laser welding. Also, the sealed terminal device includes a lead-through conductor.

11 Claims, 9 Drawing Sheets

RIGID ENDOSCOPE WITH HERMETIC SEAL

CROSS-REFERENCE TO RELATED APPLICATION

This application claims priority under 35 USC 119 from Japanese Patent Application No. 2014-038851, filed 28 Feb. 2014, the disclosure of which is incorporated by reference herein.

BACKGROUND OF THE INVENTION

1. Field of the Invention

The present invention relates to a rigid endoscope with hermetic seal. More particularly, the present invention relates to a rigid endoscope of which a hermetic shell in a rigid tube can be sealed reliably with a simple structure.

2. Description Related to the Prior Art

A rigid electronic endoscope includes a rigid tube or endoscope tube and a grip handle. The rigid tube is used for entry in a body cavity of a patient. The grip handle is disposed at a proximal end of the rigid tube. The grip handle is connected to a light source apparatus for supply of light and to a processing apparatus for forming an image of an object. The rigid tube has a tip device. Window components (window plates) are provided in the tip device, including lighting window components and a viewing window component. The lighting window components apply light to the object. The viewing window component receives image light from the object. A light guide device as a fiber bundle constituted by bundling plural optical fibers has an exit end, which is opposed to the lighting window components. An imaging module is disposed behind the viewing window component, and includes a lens system for focusing and an image sensor. The light guide device extends from the rigid tube to the grip handle, and guides light from the light source apparatus to the lighting window components. The lens system focuses image light from an object in the body cavity on the image sensor upon receiving the image light through the viewing window component. The image sensor generates the image of the object and outputs an image signal. The processing apparatus forms a video image according to the image signal from the image sensor, and causes a display panel to display the image.

The rigid endoscope after use is sterilized for the purpose of preventing infection due to repeated use. An example of the sterilization is autoclave sterilization by use of saturated water vapor at high temperature and high pressure. JP-A 7-039515 discloses the rigid endoscope with suitable firmness with resistance in the presence of the saturated water vapor at high temperature and high pressure.

In the rigid endoscope of JP-A 7-039515, the lens system (objective lens) is kept positioned on a lens holder with seal packing. The image sensor (CCD) is attached to a holder positioned at the rear end of the lens holder. Resin encapsulant is provided on the surface of the lens holder and the holder, to seal the imaging module air-tightly to prevent entry of the saturated water vapor at high temperature and high pressure.

A method of sealing the imaging module is the use of the encapsulant in JP-A 7-039515. In addition, other methods of the sealing are available, for example, the imaging module is contained in a distal portion of a stainless hermetic shell of a cylindrical shape, and a sealed terminal device seals a proximal end of the hermetic shell.

In FIGS. 9A and 9B, a structure of sealing a proximal end of the hermetic shell is illustrated. An endoscope has an imaging module (not shown), a hermetic shell 201 (case or container), and a sealed terminal device 200 or lead-through device (sealing closure device). The hermetic shell 201 contains the imaging module. The sealed terminal device 200 is attached to a proximal end of the hermetic shell 201. The sealed terminal device 200 encloses the hermetic shell 201 hermetically, and also operates to wiring of connecting lines (not shown) from the imaging module to the outside of the hermetic shell 201 in a sealed state. The sealed terminal device 200 includes an outer ring 202 or outer frame, insulating encapsulant 203, and lead-through conductors 204 (terminal pins). The insulating encapsulant 203 is disposed in the outer ring 202. The lead-through conductors 204 are set through the insulating encapsulant 203, and encapsulated with the insulating encapsulant 203 for electrical conduction from the imaging module to the outside of the hermetic shell 201.

A receiving opening 205 or inner wall (female type) is formed in a proximal end of the hermetic shell 201. A plug head 206 (male type) is defined with the sealed terminal device 200. The plug head 206 is fitted in the receiving opening 205 in a male/female coupling arrangement, to combine the sealed terminal device 200 with the proximal end of the hermetic shell 201.

The receiving opening 205 is cylindrical like the hermetic shell 201, and contains the plug head 206. The receiving opening 205 includes an inner surface 207 and a first edge surface 208. The inner surface 207 extends in the axial direction of the plug head 206 relative to the receiving opening 205. The first edge surface 208 is an end surface of the hermetic shell 201 perpendicular to the inner surface 207. Also, the plug head 206 is cylindrical and entered in the receiving opening 205. The plug head 206 includes an outer surface 209 and a second edge surface 210. The outer surface 209 extends in the axial direction, and is opposed to the inner surface 207. The second edge surface 210 is erect from the outer surface 209, and contacted by the first edge surface 208. The second edge surface 210 is a shoulder portion around the outer surface 209, and regulates an entry amount of the plug head 206 into the receiving opening 205 by contacting the first edge surface 208. An outer diameter $\Phi 1$ of the outer surface 209 is set finely smaller than an inner diameter $\Phi 2$ of the inner surface 207 for the purpose of smoothing entry of the plug head 206 into the receiving opening 205.

For fitting the plug head 206 in the receiving opening 205, the plug head 206 is pushed into the receiving opening 205 in the axial direction while the outer surface 209 is guided by the inner surface 207 of the receiving opening 205 until the first edge surface 208 comes in contact with the second edge surface 210 in FIG. 9B. As the outer diameter $\Phi 1$ of the outer surface 209 is finely smaller than the inner diameter $\Phi 2$ of the inner surface 207, there occurs a small clearance between the inner and outer surfaces 207 and 209. In view of this, the inner and outer surfaces 207 and 209 are welded together by laser welding at a weld area WP0 and a dotted circle near to the first and second edge surfaces 208 and 210 after fitting the plug head 206 in the receiving opening 205. Thus, the hermetic shell 201 can be closed air-tightly.

The size of the clearance between the inner and outer surfaces 207 and 209 influences to an amount of heat transmitted between those by the laser. Should the clearance be too wide, welding will be insufficient due to the low amount of the transmitted heat. No hermeticity is obtained because no firm attachment is obtained between the receiving opening 205 and the plug head 206. Furthermore, the sealed terminal device 200 may be dropped away from the hermetic shell 201 by damage of the weld area. Should the clearance be too narrow, welding will be excessive due to the high amount of the transmitted heat. Hermeticity is lost because the sealed terminal device 200 is overmelted to break the insulating encapsulant 203 in the outer ring 202. It is necessary in the laser welding to regularize the size of the clearance between the inner and outer surfaces, 207 and 209 to regulate an amount of the transmitted heat of laser from the inner surface 207 to the outer surface 209.

In FIGS. 9A and 9B, the inner and outer surfaces 207 and 209 of the receiving opening 205 and the plug head 206 are directed in the axial direction of the plug head 206. It is necessary to increase precision of an outer diameter $\Phi 1$ of the outer surface 209 and an inner diameter $\Phi 2$ of the inner surface 207 for regularizing the size of the clearance between the inner and outer surfaces 207 and 209. However, the sizes of the sealed terminal device 200 and the hermetic shell 201 are as small as several millimeters, because of an outer diameter of 3 mm or so. It is very difficult to obtain the outer diameter $\Phi 1$ of the outer surface 209 and the inner diameter $\Phi 2$ of the inner surface 207 at a high precision. The size of the clearance between the inner and outer surfaces 207 and 209 cannot be easily regularized. Possibility of ensuring hermeticity of the hermetic shell 201 with the sealed terminal device 200 is low, to decrease the yield of the product.

SUMMARY OF THE INVENTION

In view of the foregoing problems, an object of the present invention is to provide a rigid endoscope of which a hermetic shell in a rigid tube can be sealed reliably with a simple structure.

In order to achieve the above and other objects and advantages of this invention, a rigid endoscope includes an image sensor for imaging an object in a body cavity. A lens system focuses image light from the object on the image sensor. An imaging module has the image sensor and the lens system incorporated therein. A hermetic shell is disposed tubularly to extend in an axial direction, for containing the imaging module. A receiving opening is formed in the hermetic shell at a proximal end in the axial direction. A female tapered surface is formed inside the receiving opening. A sealed terminal device hermetically closes the receiving opening. A male tapered surface is formed on the sealed terminal device, for engagement with the female tapered surface, to keep the hermetic shell air-tight.

Preferably, the male and female tapered surfaces are attached together by laser welding.

Preferably, the sealed terminal device includes a lead-through conductor for connecting a connecting line inside the hermetic shell to a cable line outside the hermetic shell. A supporting insulator has the male tapered surface, for supporting the lead-through conductor.

Preferably, the supporting insulator includes an outer ring having the male tapered surface. Insulating encapsulant is disposed in the outer ring, for encapsulating the lead-through conductor.

Preferably, a sectional shape of the male and female tapered surfaces with reference to the axial direction is linear.

Preferably, taper angles of the male and female tapered surfaces with reference to the axial direction are equal to one another.

In another preferred embodiment, a sectional shape of the male and female tapered surfaces with reference to the axial direction is curved.

Preferably, a minimum outer diameter of the male tapered surface is smaller than a minimum inner diameter of the female tapered surface.

In still another preferred embodiment, a minimum outer diameter of the male tapered surface is larger than a minimum inner diameter of the female tapered surface.

Preferably, furthermore, a viewing window component is disposed on a distal side of the lens system, mounted on the hermetic shell hermetically, for passing the image light toward the lens system.

Preferably, the hermetic shell includes a first shell component for containing the image sensor. A second shell component is disposed on a proximal side of the first shell component, and has the receiving opening.

Preferably, furthermore, a connecting line is contained in the hermetic shell, has first and second ends, the first end being connected to the imaging module, the second end being connected to the sealed terminal device.

Consequently, a hermetic shell in a rigid tube can be sealed reliably with a simple structure, because the male and female tapered surfaces can be combined and sealed for reliable hermeticity.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

1st Embodiment

Figure 1:
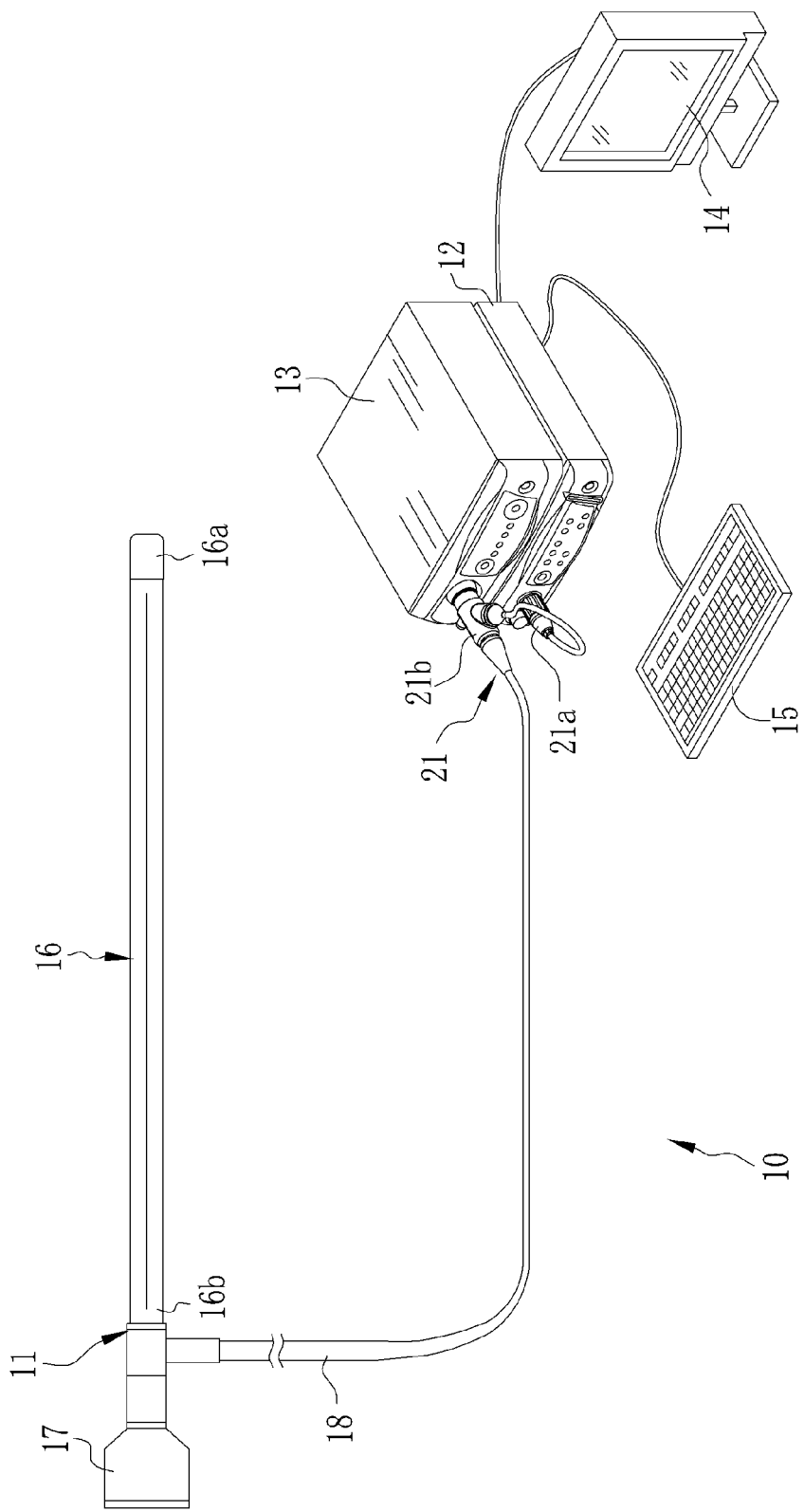
FIG. 1 is an explanatory view illustrating an endoscope system.

In FIG. 1, an endoscope system 10 includes a rigid electronic endoscope 11, a processing apparatus 12, a light source apparatus 13 and a monitor display panel 14. The rigid endoscope 11 images an object of interest in a body cavity of a patient. The processing apparatus 12 generates an image according to an image signal of the object from the rigid endoscope 11. The light source apparatus 13 supplies the rigid endoscope 11 with light for illuminating the object to be imaged. The monitor display panel 14, for example, a liquid crystal display panel, displays the image. A user input interface 15 is connected with the processing apparatus 12, for example, a keyboard, mouse and the like.

The rigid endoscope 11 includes a rigid tube 16 or endoscope tube, a grip handle 17 and a universal cable 18. The rigid tube 16 is used for entry in an abdominal cavity of a patient. The grip handle 17 is disposed at a proximal end 16b of the rigid tube 16. The universal cable 18 is disposed to extend from the grip handle 17. The universal cable 18 connects the rigid endoscope 11 to the processing apparatus 12 and the light source apparatus 13.

Figure 2:
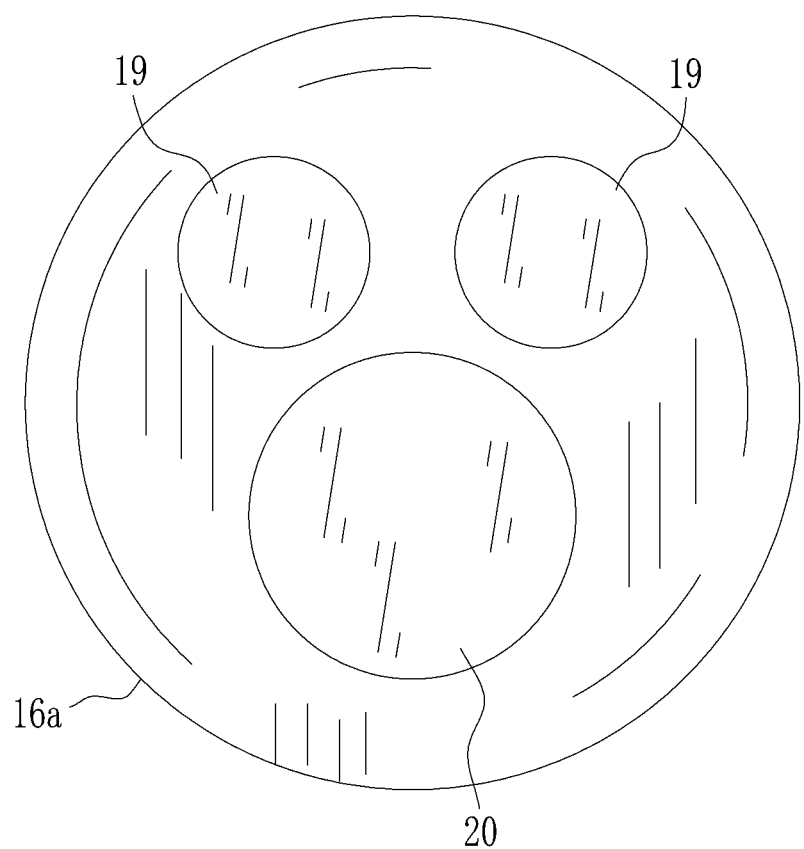
FIG. 2 is a plan illustrating a distal end of a rigid endoscope.

In FIG. 2, the rigid tube 16 has a tip device 16a. Window components (window plates) are provided in the tip device 16a, including lighting window components 19 and a viewing window component 20. The lighting window components 19 apply light to body tissue. The viewing window component 20 receives image light from the body tissue. An example of the viewing window component 20 is a plate of sapphire glass of a transparent form without color.

A composite connector 21 is disposed at a rear end of the universal cable 18 directed to the processing apparatus 12 and the light source apparatus 13. The composite connector 21 is a composite device including a first connector plug 21a for the processing apparatus 12, and a second connector plug 21b for the light source apparatus 13. The connector plugs 21a and 21b are respectively coupled with the processing apparatus 12 and the light source apparatus 13 in a removable manner.

Figure 3:
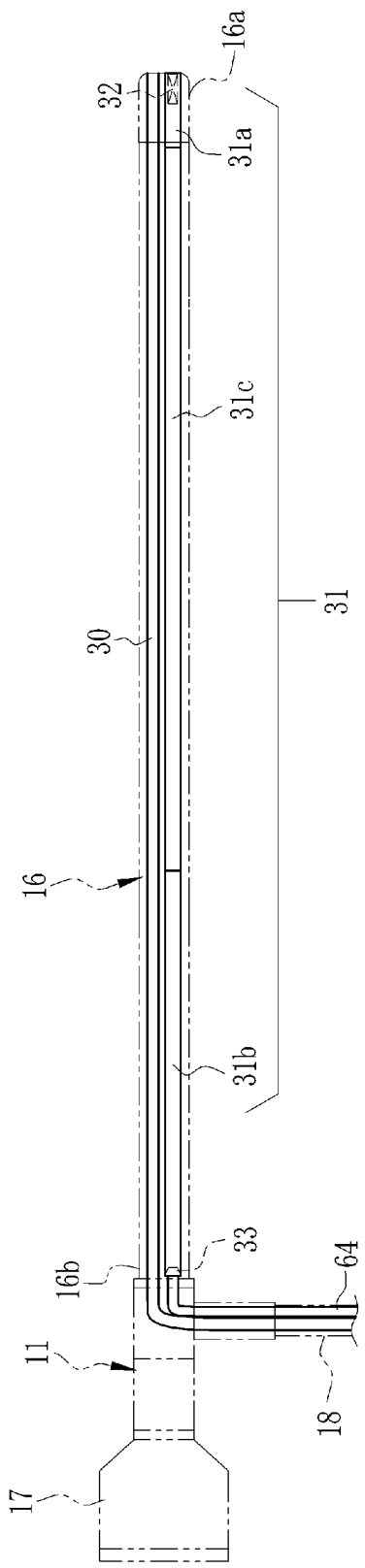
FIG. 3 is a side elevation illustrating elements incorporated in the rigid endoscope.
Figure 4:
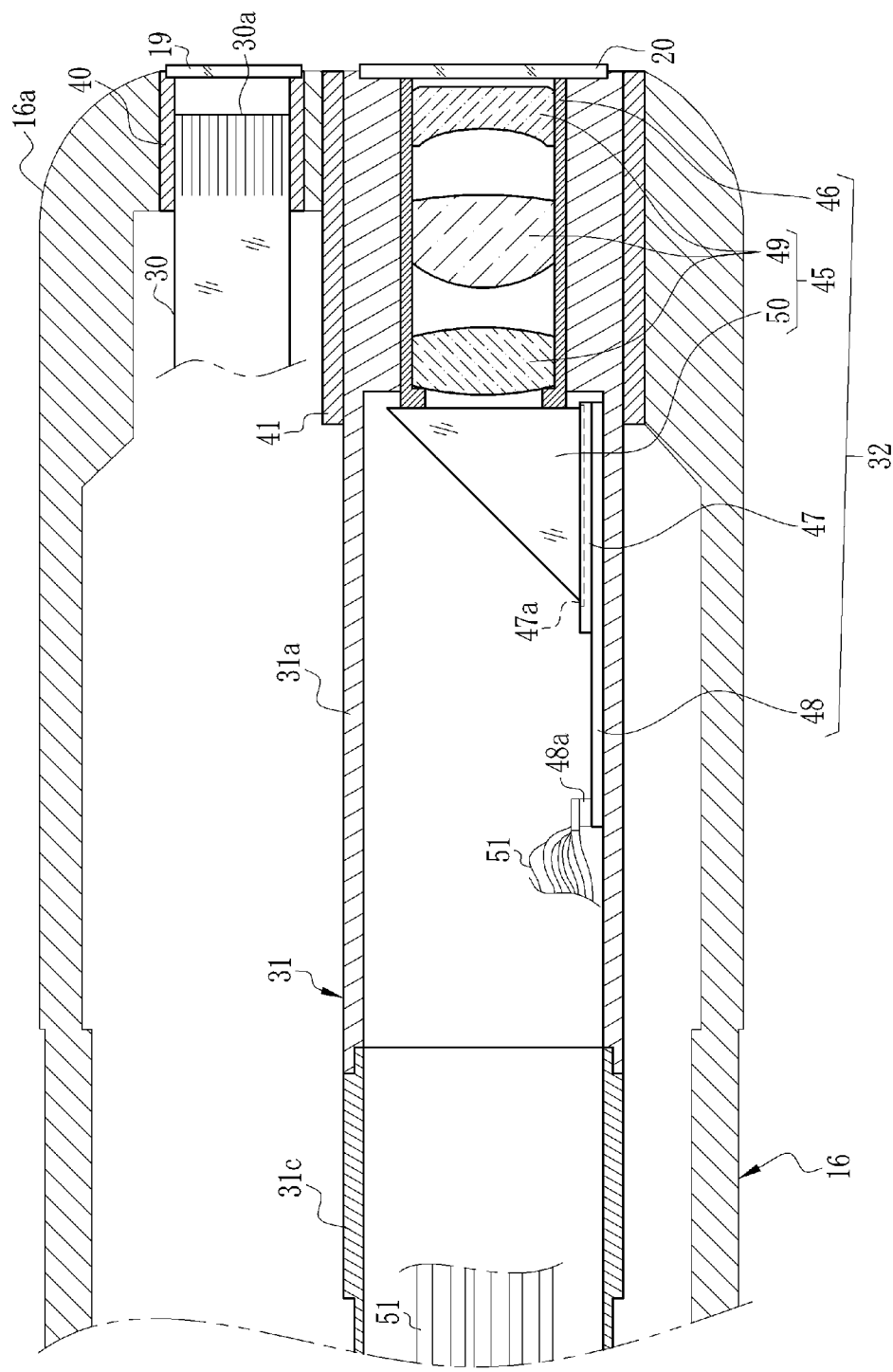
FIG. 4 is a vertical section illustrating the distal end of a rigid tube.

In FIG. 3, a light guide device 30 and a hermetic shell (case or container) 31 are contained in the rigid tube 16 and extends through the tip device 16a and the proximal end 16b. The light guide device 30 is a fiber bundle constituted by bundling plural optical fibers. The light guide device 30 further extends in a tube of the universal cable 18. An entrance end of the light guide device 30 is disposed in the second connector plug 21b. An exit end 30a of the light guide device 30 of FIG. 4 is directed to the lighting window components 19. In case the light source apparatus 13 in connection with the second connector plug 21b is driven, light from the light source apparatus 13 travels to the entrance end of the light guide device 30. The light is guided by the light guide device 30 and exits through the exit end 30a, and becomes applied to body tissue through the lighting window components 19. Note that two branches of the light guide device 30 are provided upstream of the lighting window components 19 for guiding light to the lighting window components 19.

The hermetic shell 31 includes a first shell component 31a, a second shell component 31b and an intermediate sleeve 31c. The first shell component 31a (cover sleeve) is disposed at the tip device 16a. The second shell component 31b (cover sleeve) is disposed at the proximal end 16b. The intermediate sleeve 31c connects the first shell component 31a to the second shell component 31b. Each one of the first and second shell components 31a and 31b and the intermediate sleeve 31c is a straight pipe of stainless steel in a cylindrical shape. For the connections, joint ends of the first shell component 31a and the intermediate sleeve 31c and those of the intermediate sleeve 31c and the second shell component 31b are attached together by laser welding.

An imaging module 32 or imaging unit is contained in a distal portion of the first shell component 31a of the hermetic shell 31. A sealed terminal device 33 or lead-through device (sealing closure device) is fitted in a proximal end of the second shell component 31b of the hermetic shell 31. The sealed terminal device 33 closes the hermetic shell 31 hermetically to keep air-tightness.

In FIG. 4, a holder 40 or frame is disposed in the tip device 16a. The lighting window components 19 and the exit end 30a of the light guide device 30 are aligned with one another, and fitted in the holder 40. A holder 41 or frame is disposed in the tip device 16a. A tip of the hermetic shell 31 is fitted in the holder 41. Adhesive agent is used to attach the lighting window components 19, the exit end 30a of the light guide device 30 and the hermetic shell 31 to the holders 40 and 41.

The viewing window component 20 is attached to a distal end of the hermetic shell 31 by reflow soldering of vacuum soldering. The viewing window component 20 closes the distal end of the hermetic shell 31 air-tightly. The imaging module 32 is disposed behind the viewing window component 20. The imaging module 32 includes a lens system 45 for focusing, a lens barrel 46, an image sensor 47 and a circuit board 48.

The lens system 45 includes lens optics 49 and a prism 50. Image light from the viewing window component 20 becomes incident upon the lens system 45, and focused to an active pixel area 47a of the image sensor 47 by the lens system 45. The lens barrel 46 contains the lens optics 49. An entrance surface of the prism 50 is attached to a proximal end of the lens barrel 46 by adhesive agent. An exit surface of the prism 50 is attached to the active pixel area 47a by adhesive agent. The prism 50 refracts the image light of the object from the lens optics 49 with an angle of 90 degrees, and directs the image light toward the active pixel area 47a of the image sensor 47.

The image sensor 47 is a CCD image sensor (charge coupled device image sensor). The active pixel area 47a has N×M pixels in plural arrays by use of photoconductors, such as photo diodes. For example, N=1,080 and M=1,920. The image sensor 47 is a color image sensor. Micro color filters are arranged on the active pixel area 47a with three primary colors of blue (B), green (G) and red (R). An example of the arrangement of the micro color filters is a Bayer arrangement. Note that the image sensor 47 may be a CMOS image sensor (complementary metal oxide semiconductor image sensor).

The image sensor 47 photoelectrically converts light received by the active pixel area 47a, and stores signal charge in pixels according to a light amount of the light. The signal charge is read out by a vertical scanner to a horizontal scanner by one pixel row. The signal charge read out to the horizontal scanner is converted into a voltage signal by an amplifier. The voltage signal is output by the image sensor 47 to the circuit board 48 as an image signal.

The circuit board 48 has an AFE or analog front end (not shown). The AFE processes an image signal of the analog form from the image sensor 47 in the correlated double sampling, and removes noise due to resetting the signal charge. Then the AFE amplifies the image signal after the correlated double sampling, and converts the image signal into a digital image signal having a gradation value according to a predetermined number of bits, for example, 10 bits.

A signal terminal 48a is provided at a proximal end of the circuit board 48. Connecting lines 51 or signal cables are contained in the hermetic shell 31, and has a first end (distal end) coupled to the signal terminal 48a by soldering and electrically connected to the circuit board 48. A digital image signal generated by the AFE is transmitted by the signal terminal 48a and the connecting lines 51 to the processing apparatus 12. The processing apparatus 12 processes the transmitted image signal by image processing of various functions, such as pixel interpolation, white balancing, edge enhancement and the like, and generates a video signal. The processing apparatus 12 drives the monitor display panel 14 to display the image of the video signal.

The connecting lines 51 extend to the proximal end of the hermetic shell 31. The connecting lines 51 transmit the image signal to the processing apparatus 12, and also transmit control signals from the processing apparatus 12. Examples of the control signals are a clock signal for driving the image sensor 47 at a predetermined period, and gain (amplification factor) of automatic gain control in the AFE. The image sensor 47 outputs the image signal to the AFE at a predetermined frame rate, for example, 60 frames per second, in compliance with the control signals from the processing apparatus 12.

Figure 5:
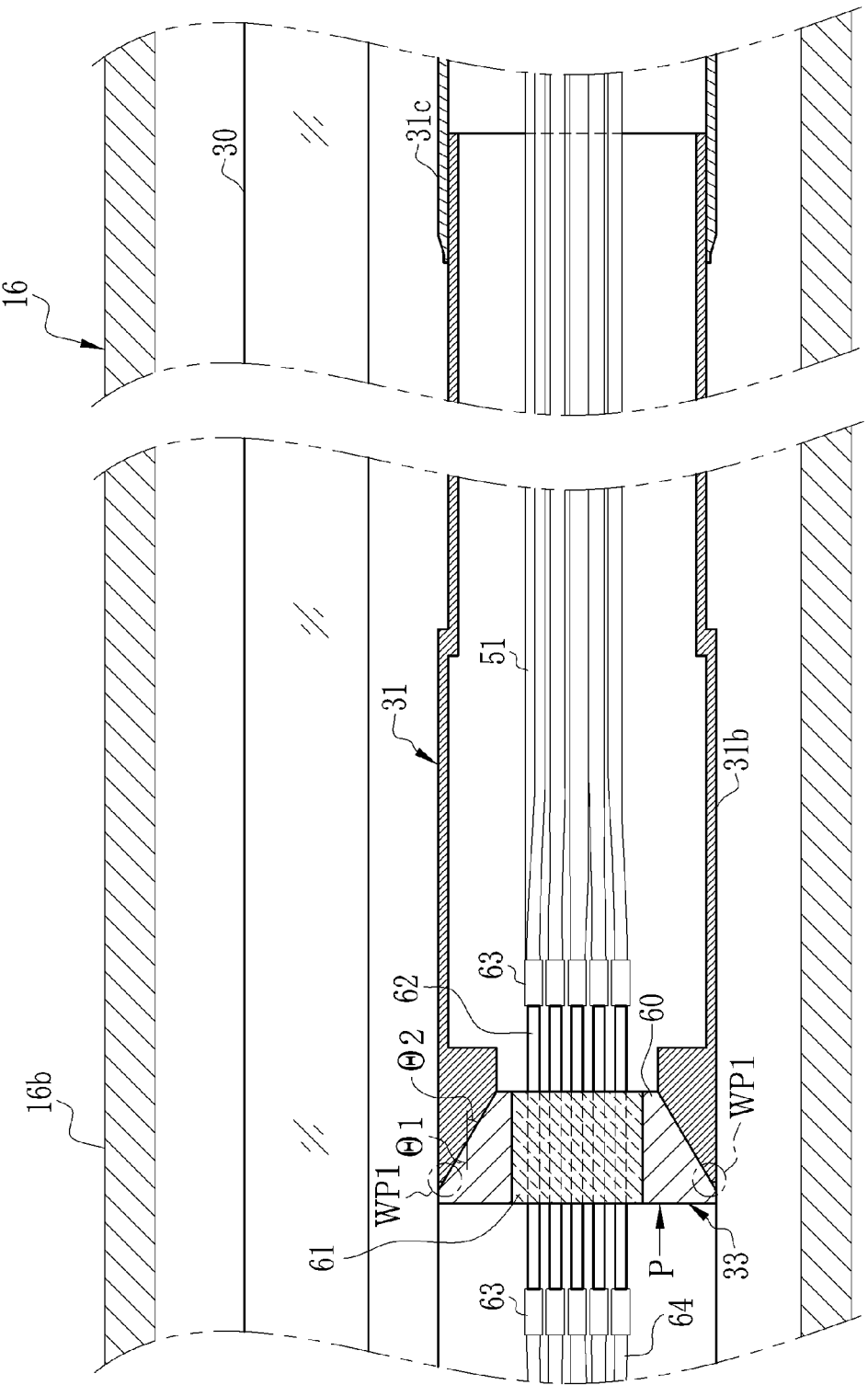
FIG. 5 is a vertical section, partially broken, illustrating a proximal end of the rigid tube.

In FIG. 5, the sealed terminal device 33 includes an outer ring 60 or outer frame, insulating encapsulant 61 (supporting insulator) and lead-through conductors 62 (terminal pins). The insulating encapsulant 61 is disposed in the outer ring 60. The lead-through conductors 62 are kept fixed in the outer ring 60 by encapsulation with the insulating encapsulant 61. Materials for those elements are heat-resistant materials for ensuring air-tightness in the hermetic shell 31 even in the environment of the sterilization with high pressure and vapor. For example, a material for the outer ring 60 and the lead-through conductors 62 is COBAL (trade name) or an alloy of iron, nickel and cobalt. The insulating encapsulant 61 is formed from borosilicate glass. A maximum outer diameter of the outer ring 60 is approximately 2.8 mm, and equal to an outer diameter of the hermetic shell 31. A length of the sealed terminal device 33 inclusive of the lead-through conductors 62 is approximately 3.9 mm. An outer diameter of the lead-through conductors 62 is 0.15 mm.

The lead-through conductors 62 are arranged at a regular interval in a radial direction of the insulating encapsulant 61. For example, the lead-through conductors 62 are 15 pins. See FIG. 6. The insulating encapsulant 61 supports the lead-through conductors 62 in a spaced manner from one another without short-circuiting with one another. An example of the regular interval (pitch) between the lead-through conductors 62 is 0.3 mm.

The lead-through conductors 62 are connectable with inner and outer wire lines disposed with the hermetic shell 31. Copper sleeves 63 are associated with ends of the lead-through conductors 62. Tips of the connecting lines 51 in the hermetic shell 31 are attached to the copper sleeves 63 by soldering, to connect the imaging module 32 to the wire lines outside the hermetic shell 31.

A second end (proximal end) of the connecting lines 51 from the circuit board 48 is connected to a first end of the lead-through conductors 62 inside the hermetic shell 31. Cable lines 64 are connected to a second end of the lead-through conductors 62 outside the hermetic shell 31. In FIG. 3, the cable lines 64 extend through the grip handle 17 and a tube of the universal cable 18. A rear end of the cable lines 64 is disposed in the first connector plug 21a. In case the first connector plug 21a is connected with the processing apparatus 12 and the processing apparatus 12 starts up, then an image signal and control signal are transmitted between the rigid endoscope 11 and the processing apparatus 12 by the connecting lines 51 and the cable lines 64.

Figure 6:
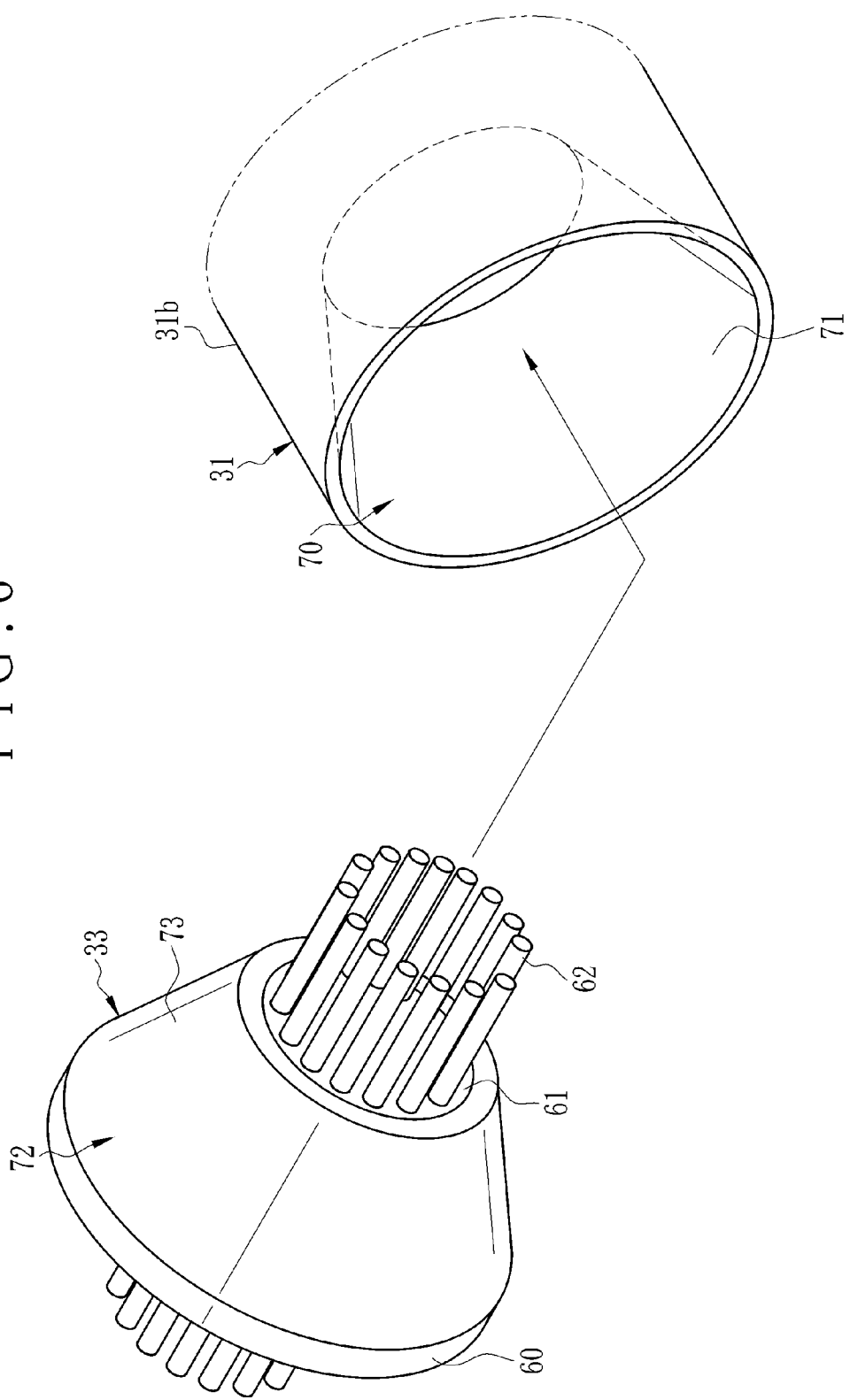
FIG. 6 is an exploded perspective view illustrating a proximal end of a hermetic shell and a sealed terminal device.

In FIG. 6, a receiving opening 70 or concave wall (female type) is defined in a proximal end of the hermetic shell 31 for partial coupling of the sealed terminal device 33. A female tapered surface 71 as a concave wall (female type) is included in the receiving opening 70, and tapered to decrease its bore in the distal direction of the hermetic shell 31. A plug head 72 (male type) is formed on a distal end of the sealed terminal device 33 for coupling to the receiving opening 70 of the hermetic shell 31. A maximum outer diameter of the plug head 72 is larger than a minimum inner diameter of the receiving opening 70 so as to keep the plug head 72 in the receiving opening 70 without drop. A male tapered surface 73 is included in the plug head 72.

The male tapered surface 73 is inclined in the same direction as the female tapered surface 71 in a male/female coupling arrangement. An outer diameter of the male tapered surface 73 decreases toward the distal end of the sealed terminal device 33. As viewed in a vertical section, the shapes of the male and female tapered surfaces 71 and 73 are linear with respect to the axial direction of the receiving opening 70 and the plug head 72. In short, those surfaces are conical. A taper angle $\Theta 1$ of the female tapered surface 71 is equal to a taper angle $\Theta 2$ of the male tapered surface 73 with reference to the axial direction. See FIG. 5. Also, the female tapered surface 71 as a guide facilitates entry of the sealed terminal device 33 into the proximal end of the hermetic shell 31.

The operation of assembling parts of the hermetic shell 31 is described now. At first, the imaging module 32 at the first end of the connecting lines 51 is attached to the distal end of the first shell component 31a of the hermetic shell 31. Then the connecting lines 51 are entered through the intermediate sleeve 31c. Joint ends of the first shell component 31a and the intermediate sleeve 31c are welded together by laser welding. Similarly, the connecting lines 51 are entered through the second shell component 31b. Joint ends of the second shell component 31b and the intermediate sleeve 31c are welded together by laser welding.

Then the second end of the connecting lines 51 protruded from the proximal end of the second shell component 31b is attached to the copper sleeves 63 by soldering at the end of the lead-through conductors 62 on the plug head 72 for containment in the hermetic shell 31. Also, the cable lines 64 are attached to the copper sleeves 63 by soldering at an end of the lead-through conductors 62 on a side opposite to the plug head 72 outside the hermetic shell 31.

Then the male tapered surface 73 of the sealed terminal device 33 is guided by the female tapered surface 71 of the hermetic shell 31 after soldering of the connecting lines 51 and the cable lines 64. The sealed terminal device 33 is pushed into the proximal end of the hermetic shell 31 as indicated by the arrow in FIG. 6. The male and female tapered surfaces 71 and 73 are attached together by laser welding at the joint ends of the sealed terminal device 33 and the proximal end of the hermetic shell 31 as indicated by the circle at a sign WP1 in FIG. 5. The proximal end of the hermetic shell 31 is hermetically closed to keep the hermetic shell 31 air-tight.

In the hermetic shell 31, the weld area WP1 is predetermined, and has a thickness of 0.1-0.2 mm. The laser welding is carried out locally for a short time to the weld area WP1 so that remaining portions of the hermetic shell 31 will not be heated or melted accidentally.

After the use, the rigid endoscope 11 is moved into a sterilizing apparatus with high pressure and vapor, and sterilized. The viewing window component 20 and the sealed terminal device 33 keep the hermetic shell 31 enclosed hermetically, and prevent entry of saturated water vapor of high temperature and high pressure into the hermetic shell 31. Thus, it is possible to keep the imaging module 32 and the connecting lines 51 safe without breakage or degradation in the presence of the saturated water vapor.

The receiving opening 70 with the female tapered surface 71 is disposed at the proximal end of the hermetic shell 31. The plug head 72 with the male tapered surface 73 tapered in the same direction as the female tapered surface 71 is disposed with the sealed terminal device 33. Thus, no gap space is created between the male and female tapered surfaces 71 and 73 upon fitting the sealed terminal device 33 in the hermetic shell 31 by engaging the receiving opening 70 with the plug head 72.

Figure 9A:
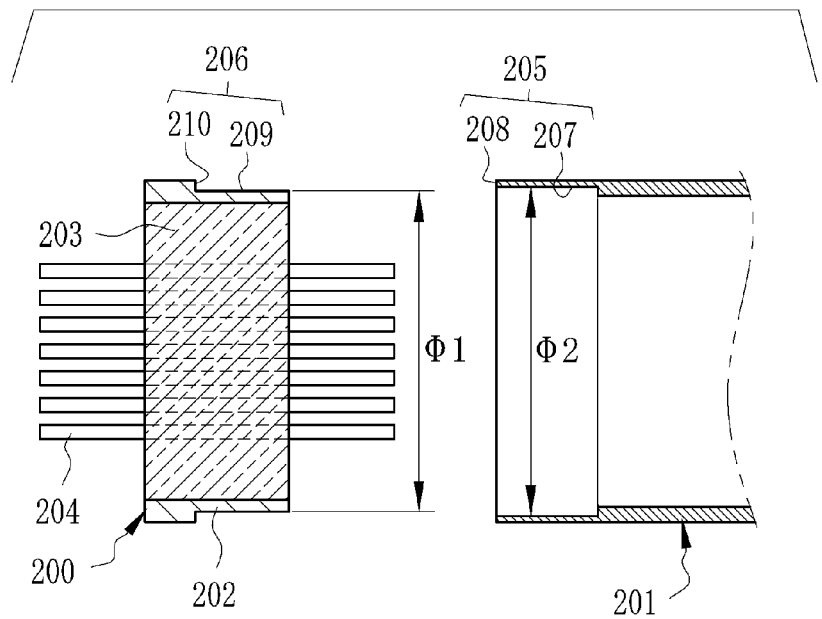
FIG. 9A is a vertical section illustrating a hermetic shell and a sealed terminal device of a known endoscope.
Figure 9B:
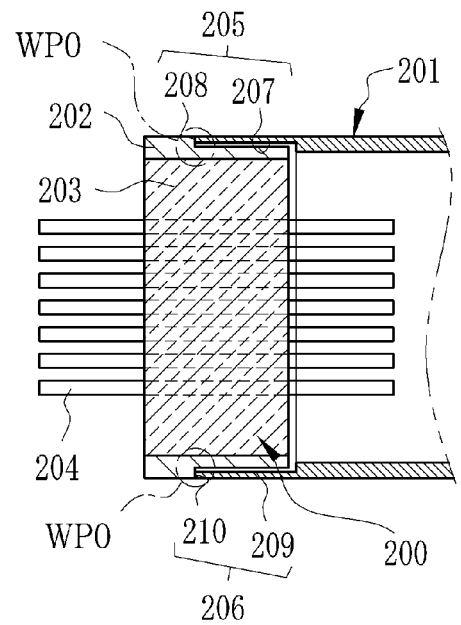
FIG. 9B is a vertical section illustrating the same as FIG. 9A in a combined state.

In the known structure of FIGS. 9A and 9B, welding may be insufficient due to shortage in an amount of heat of laser from an inner surface 207 to an outer surface 209 according to irregularity in an interval between those. Hermeticity may be lost due to weakness in the connection between a receiving opening 205 or inner wall (female type) and a plug head 206 (male type). A sealed terminal device 200 or lead-through device (sealing closure device) may be dropped away due to breakage of the weld area. Insulating encapsulant 203 may be damaged by excessive melting of the sealed terminal device 200 with too high a heat amount in the welding. However, the female tapered surface 71 in the present invention can be reliably welded to the male tapered surface 73. The laser welding is possible constantly with suitable power without damaging the insulating encapsulant 61. Good yield is possible with high possibility in ensuring hermeticity of the hermetic shell 31 with the sealed terminal device 33. Also, the female tapered surface 71 can be welded to the male tapered surface 73 with a comparatively low power.

It is easy to form the receiving opening 70 in the hermetic shell 31 internally with the female tapered surface 71. Also, it is easy to form the plug head 72 on the sealed terminal device 33 peripherally with the male tapered surface 73. Producing the receiving opening 70 and the plug head 72 is easier than producing the receiving opening 205 and the plug head 206 in FIGS. 9A and 9B.

As the female tapered surface 71 operates also for guiding the sealed terminal device 33 toward the inside of the hermetic shell 31, coupling of the receiving opening 70 with the plug head 72 can be smooth with high operability.

Figure 7A:
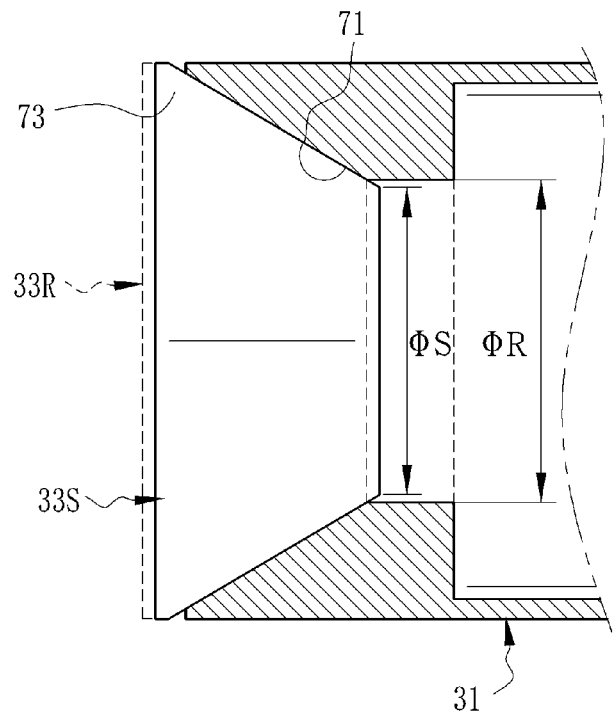
FIG. 7A is a vertical section illustrating the hermetic shell and another preferred sealed terminal device of a smaller size.

No gap occurs between the male and female tapered surfaces 71 and 73 even with insufficient precision in their production. In FIG. 7A, an example of a sealed terminal device 33S or lead-through device (sealing closure device) is illustrated. The sealed terminal device 33S has a minimum outer diameter ΦS of the male tapered surface 73 smaller than a minimum outer diameter ΦR of the male tapered surface 73 of a sealed terminal device 33R or lead-through device of a normal shape indicated by the dotted line (namely, minimum inner diameter of the female tapered surface 71). The sealed terminal device 33S is pushed in to a finely larger extent in the distal direction of the hermetic shell 31 than the sealed terminal device 33R in its engagement position. So the female tapered surface 71 is tightly fitted on the male tapered surface 73 without a gap.

Figure 7B:
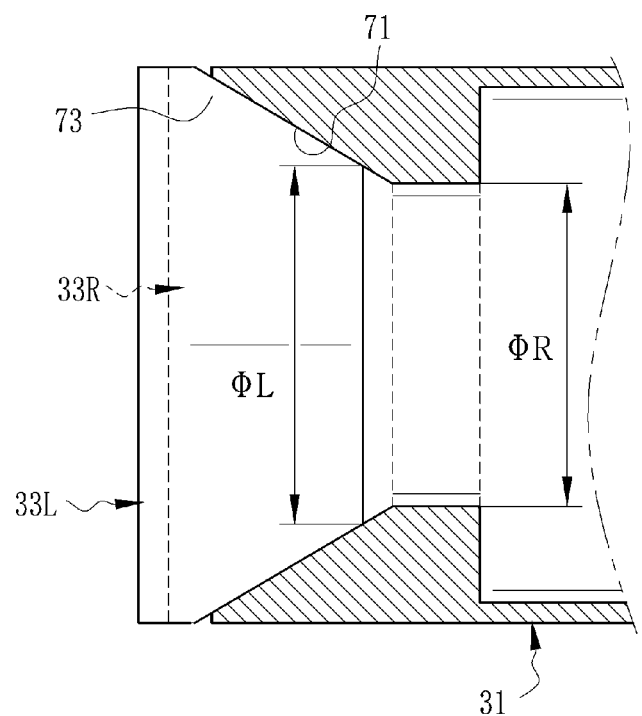
FIG. 7B is a vertical section illustrating the hermetic shell and still another preferred sealed terminal device of a larger size.

In FIG. 7B, a sealed terminal device 33L or lead-through device is illustrated. A minimum outer diameter ΦL of the male tapered surface 73 is larger than the minimum outer diameter ΦR of that of the sealed terminal device 33R of the normal type. A proximal end of the sealed terminal device 33L protrudes finely from a proximal position of the sealed terminal device 33R, but the female tapered surface 71 becomes tightly engaged with the male tapered surface 73. Also, the male and female tapered surfaces 71 and 73 are regularly conical of a form facilitating production. Thus, there is no requirement of much time or labor for further raising precision in producing the male and female tapered surfaces 71 and 73. Note that the lead-through conductors 62 and the connecting lines 51 are omitted from FIGS. 7A and 7B for clarification.

In the course of the sterilization with high pressure and vapor, outer pressure is applied to the sealed terminal device 33 in an inward direction. Force is applied to the sealed terminal device 33 for push in a distal direction of the hermetic shell 31 as indicated by the arrow P in FIG. 5. The force is applied by the male tapered surface 73 to the female tapered surface 71 having the decreasing diameter. Thus, the engagement between the male and female tapered surfaces 71 and 73 and between the hermetic shell 31 and the sealed terminal device 33 is tightened. The air-tightness of the hermetic shell 31 can be reliable.

As the sealed terminal device 33 is constituted by the outer ring 60, the insulating encapsulant 61 and the lead-through conductors 62, the connecting lines 51 in the hermetic shell 31 can be readily connected with the cable lines 64 by the sealed terminal device 33 even in the hermetically enclosed state of the hermetic shell 31.

As the hermetic shell 31 is constituted by the first shell component 31a containing the imaging module 32 and the second shell component 31b where the sealed terminal device 33 is disposed, operability in assembling the imaging module 32 can be higher than a structure of a single piece of pipe for the hermetic shell 31.

Furthermore, it is possible to form male and female tapered surfaces at joint ends of the first shell component 31a and the intermediate sleeve 31c or at joint ends of the second shell component 31b and the intermediate sleeve 31c in a similar manner to the male and female tapered surfaces of the hermetic shell 31 and the sealed terminal device 33. Note that those joint ends have no elements easily breakable with an excessive state of the welding in the manner of the insulating encapsulant 61 of the sealed terminal device 33. Thus, effect of the male and female tapered surfaces at the joint ends of the first shell component 31a and the intermediate sleeve 31c or at the joint ends of the second shell component 31b and the intermediate sleeve 31c is auxiliary in view of their purpose.

2nd Embodiment

Figure 8:
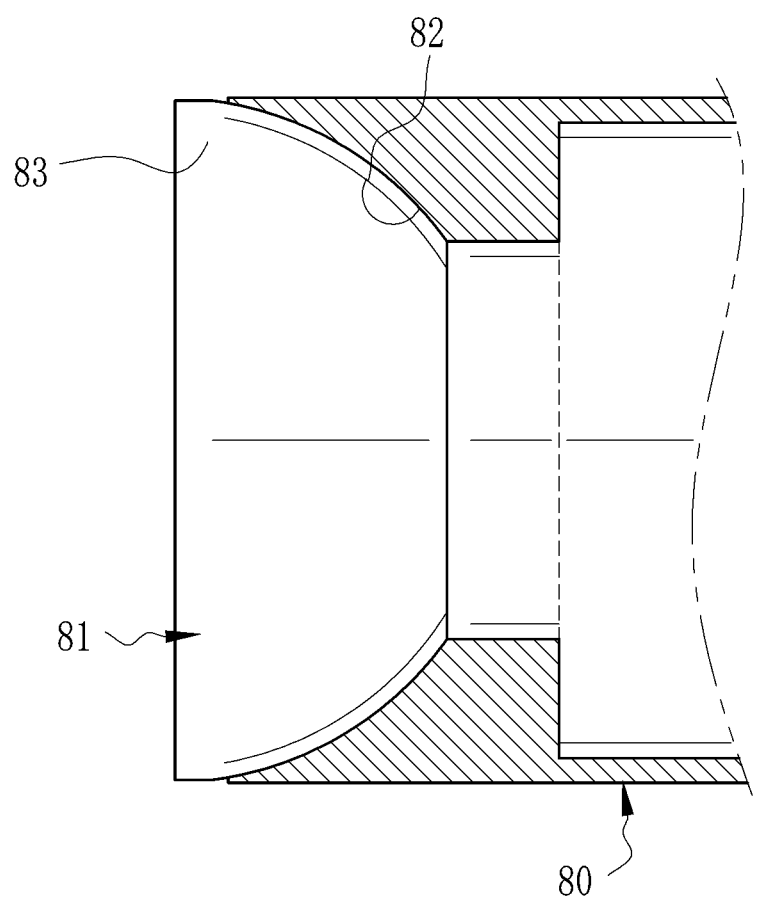
FIG. 8 is a vertical section illustrating another preferred hermetic shell and a sealed terminal device with hemispherical tapered surfaces.

In the above embodiment, the male and female tapered surfaces 71 and 73 are regularly conical. In FIG. 8, another preferred hermetic shell 80 (case or container) is illustrated. In a male/female coupling arrangement, a female tapered surface 82 as a concave wall (female type) of a receiving opening in the hermetic shell 80 is hemispherical. A sealed terminal device 81 or lead-through device (sealing closure device) is combined with the hermetic shell 80. A male tapered surface 83 of a plug head (male type) of the sealed terminal device 81 is hemispherical. In case the sealed terminal device 33 is fitted in the hermetic shell 31, no gap occurs between the male and female tapered surfaces 82 and 83 while the female tapered surface 82 is fitted on the male tapered surface 83. The same effect as the above embodiment can be obtained. Note that the lead-through conductors (terminal pins), connecting lines and the like are omitted from FIG. 8 in the same manner as FIGS. 7A and 7B.

In the first embodiment, the receiving opening 70 and the plug head 72 are attached together by the laser welding. However, those may be attached together by electron beam welding or the like. In the first embodiment, the hermetic shell 31 has the first and second shell components 31a and 31b and the intermediate sleeve 31c. However, the number of parts of the hermetic shell 31 may be 1, 2 or 4 or more. In the first embodiment, the first and second shell components 31a and 31b and the intermediate sleeve 31c are the straight pipes. However, the second shell component 31b may be extended to the joint end between the grip handle 17 and the universal cable 18. A proximal end of the second shell component 31b may be bent.

In the above embodiment, the taper angle Θ2 of the male tapered surface 73 is equal to the taper angle Θ1 of the female tapered surface 71 with reference to the axial direction of the plug head 72 with the receiving opening 70. However, it is possible to set the taper angle Θ2 of the male tapered surface 73 larger than the taper angle Θ1 of the female tapered surface 71. A small clearance space may be defined between the male and female tapered surfaces 71 and 73 on the distal side of the hermetic shell 31. However, the female tapered surface 71 contacts the male tapered surface 73 at the proximal end of the hermetic shell 31 with the weld area WP1, where no gap space is formed. Consequently, the same effect as the first embodiment can be obtained in the structure in which the taper angle Θ2 of the male tapered surface 73 is larger than the taper angle Θ1 of the female tapered surface 71.

In case the taper angle Θ2 of the male tapered surface 73 is set finely smaller than the taper angle Θ1 of the female tapered surface 71 with reference to the axial direction, the female tapered surface 71 contacts the male tapered surface 73 at a distal end of the sealed terminal device 33. There occurs a small gap space between those at the weld area WP1. However, there is low possibility of a difference between the taper angle Θ1 of the female tapered surface 71 and the taper angle Θ2 of the male tapered surface 73 in view of suitability for working of the male and female tapered surfaces 71 and 73. It is possible to estimate that no gap space occurs between the male and female tapered surfaces 71 and 73. Therefore, the same effect as the first embodiment can be obtained even assuming that the taper angle Θ2 of the male tapered surface 73 is set finely smaller than the taper angle Θ1 of the female tapered surface 71.

A location of containing the imaging module 32 is not limited to the distal end of the hermetic shell 31. The imaging module 32 can be contained in the intermediate sleeve of the hermetic shell 31.

In the above embodiment, the male and female tapered surfaces 71 and 73 are shaped in the form of the frustum of the cone. The male and female tapered surfaces 82 and 83 are hemispherical. However, the female tapered surface 71 and 82 and the male tapered surface 73 and 83 can be constituted by other tapered forms, for example, a form of a frustum of an elliptic cone, a form of a frustum of a pyramid, and the like.

In the above embodiment, the sealed terminal device 33 has the outer ring 60 around the insulating encapsulant 61. However, the outer ring 60 can be omitted from the sealed terminal device 33. Namely, the lead-through conductors 62 can be incorporated in the sealed terminal device 33 by molding a material for the insulating encapsulant 61 (supporting insulator) together with the lead-through conductors 62 without use of the outer ring 60.

In the above embodiments, the receiving opening 70 and the sealed terminal device 33 are disposed at the proximal end of the hermetic shell 31. However, it is possible to dispose the receiving opening 70 and the sealed terminal device 33 on a lateral wall of the hermetic shell 31.

The feature of the present invention can be used in medical apparatuses different from the rigid endoscope, for example, an ultrasonic endoscope, ultrasound echo apparatus, light delivery catheter, and other medical apparatuses. In the above embodiments, the sealed terminal device is connected to the connecting line from the imaging module. A connecting line in connection between the sealed terminal device and a medical apparatus can be a signal line for any one of transmission and reception of a signal, and a drive line for supplying power.

According to a preferred embodiment mode of the invention, a circuit apparatus having a circuit device includes a hermetic shell for containing the circuit device. A connecting line is contained in the hermetic shell, has first and second ends, the first end being connected to the circuit device. A receiving opening is formed in the hermetic shell. A female tapered surface is formed inside the receiving opening. A sealed terminal device is connected electrically with the second end of the connecting line, for hermetically closing the receiving opening. A male tapered surface is formed on the sealed terminal device, for retaining the sealed terminal device in the receiving opening by engagement with the female tapered surface, to keep the hermetic shell air-tight.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A rigid endoscope comprising:
   an image sensor for imaging an object in a body cavity;
   a lens system for focusing image light from said object on said image sensor;
   an imaging module having said image sensor and said lens system incorporated therein;
   a hermetic shell, disposed tubularly to extend in an axial direction, for containing said imaging module;
   a receiving opening formed in said hermetic shell at a proximal end in said axial direction;
   a female tapered surface formed inside said receiving opening;
   a sealed terminal device for hermetically closing said receiving opening;
   a male tapered surface, formed on said sealed terminal device, for engagement with said female tapered surface, to keep said hermetic shell air-tight.

2. A rigid endoscope as defined in claim 1, wherein said male and female tapered surfaces are attached together by laser welding.

3. A rigid endoscope as defined in claim 2, wherein said sealed terminal device includes:
   a lead-through conductor for connecting a connecting line inside said hermetic shell to a cable line outside said hermetic shell;
   a supporting insulator, having said male tapered surface, for supporting said lead-through conductor.

4. A rigid endoscope as defined in claim 3, wherein said supporting insulator includes:
   an outer ring having said male tapered surface;
   insulating encapsulant, disposed in said outer ring, for encapsulating said lead-through conductor.

5. A rigid endoscope as defined in claim 2, wherein a sectional shape of said male and female tapered surfaces with reference to said axial direction is linear.

6. A rigid endoscope as defined in claim 5, wherein taper angles of said male and female tapered surfaces with reference to said axial direction are equal to one another.

7. A rigid endoscope as defined in claim 2, wherein a sectional shape of said male and female tapered surfaces with reference to said axial direction is curved.

8. A rigid endoscope as defined in claim 2, wherein a minimum outer diameter of said male tapered surface is smaller than a minimum inner diameter of said female tapered surface.

9. A rigid endoscope as defined in claim 2, wherein a minimum outer diameter of said male tapered surface is larger than a minimum inner diameter of said female tapered surface.

10. A rigid endoscope as defined in claim 2, further comprising a viewing window component, disposed on a distal side of said lens system, mounted on said hermetic shell hermetically, for passing said image light toward said lens system.

11. A rigid endoscope as defined in claim 2, wherein said hermetic shell includes:
    a first shell component for containing said image sensor;
    a second shell component, disposed on a proximal side of said first shell component, having said receiving opening.

\* \* \* \* \*